United States Patent
Childers et al.

(10) Patent No.: US 9,101,716 B2
(45) Date of Patent: Aug. 11, 2015

(54) MULTI-PASS DIALYSIS

(75) Inventors: Robert W. Childers, Trinity, FL (US); Anthony J. Simiele, III, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 713 days.

(21) Appl. No.: 12/024,828

(22) Filed: Feb. 1, 2008

(65) Prior Publication Data
US 2009/0198170 A1 Aug. 6, 2009

(51) Int. Cl.
A61M 37/00 (2006.01)
A61M 1/28 (2006.01)
A61M 1/16 (2006.01)

(52) U.S. Cl.
CPC .............. *A61M 1/28* (2013.01); *A61M 1/1639* (2014.02); *A61M 1/1694* (2013.01); *A61M 1/1696* (2013.01)

(58) Field of Classification Search
CPC ........... A61M 1/16; A61M 1/14; B01D 61/24
USPC ........... 604/6.09, 4.01, 5.01, 6.01, 27–29, 19; 210/103, 646, 85, 143
See application file for complete search history.

(56) References Cited

U.S. PATENT DOCUMENTS

| | | |
|---|---|---|
| RE29,346 E | 8/1977 | Kopp |
| 4,486,189 A | 12/1984 | Troutner et al. |
| 4,490,134 A | 12/1984 | Troutner |
| 4,514,295 A | 4/1985 | Mathieu et al. |
| 4,552,552 A | 11/1985 | Polaschegg et al. |
| 4,690,772 A | 9/1987 | Tell et al. |
| 4,828,543 A | 5/1989 | Weiss et al. |
| 4,940,455 A * | 7/1990 | Guinn .......................... 604/6.05 |
| 5,679,775 A | 10/1997 | Boos et al. |
| 5,851,202 A * | 12/1998 | Carlsson ....................... 604/247 |
| 6,174,442 B1 | 1/2001 | Geisser et al. |
| 6,258,027 B1 | 7/2001 | Sternby |
| 6,527,735 B1 | 3/2003 | Davankov et al. |
| 6,579,460 B1 | 6/2003 | Willis et al. |
| 7,033,498 B2 | 4/2006 | Wong |

(Continued)

FOREIGN PATENT DOCUMENTS

WO  2009006489  1/2009

OTHER PUBLICATIONS

The removal of uremic toxins; Annemieke Dhondt, Raymond Vanholder, Wim Van Biesen, and Norbert Lameire; Kidney International, vol. 58, Suppl. 76 (2000), pp. S-47-S-59.

(Continued)

*Primary Examiner* — Tatyana Zalukaeva
*Assistant Examiner* — Benedict L Hanrahan
(74) *Attorney, Agent, or Firm* — K&L Gates LLP

(57) ABSTRACT

A system for dialysis is disclosed. The system uses renal failure therapy fluid, such as dialysis fluid, several times before it is discarded. In a home hemodialysis application, the patient's blood is passed through the dialyzer several times, that is, multiple passes through the dialyzer, until the dialysis fluid is saturated or near saturation, with waste products from the patient's blood. In peritoneal dialysis, the dialysate is used at least twice within the patient's peritoneal cavity, i.e., multiple passes, before it is discarded. This has the effect minimizing the amount of dialysate a patient must handle and dispose of in the dialysis process.

15 Claims, 12 Drawing Sheets

(56) References Cited

U.S. PATENT DOCUMENTS

| | | | |
|---|---|---|---|
| 7,208,092 | B2 | 4/2007 | Micheli |
| 7,241,272 | B2 | 7/2007 | Karoor et al. |
| 2002/0107474 | A1 | 8/2002 | Noack |
| 2004/0019312 | A1* | 1/2004 | Childers et al. ............... 604/4.01 |
| 2004/0019320 | A1 | 1/2004 | Childers et al. |
| 2004/0031756 | A1* | 2/2004 | Suzuki et al. ................. 210/646 |
| 2005/0131332 | A1 | 6/2005 | Kelly et al. |
| 2010/0264086 | A1* | 10/2010 | Noack et al. ................... 210/647 |

OTHER PUBLICATIONS

Near-Infrared Spectroscopy for Measuring Urea in Hemodialysis Fluids; Christopher V. Eddy and Mark A. Arnold; Clinical Chemistry 47:7, pp. 1279-1286 (2001).

Calcium balance and serum ionized calcium fluctuations in on-line haemodiafiltration in relation to ultrafiltration rate and dialysate calcium concentration; F. Malberti, B. Corradi, C. Tetta and E. Imbasciati; Nephrology Dialysis Transplantation (1994) 9: pp. 1759-1764.

International Search Report and Written Opinion for International Application No. PCT/US2009/030736 mailed on Jun. 4, 2009.

International Preliminary Report on Patentability for International Application No. PCT/US2009/030736 dated Mar. 29, 2010.

Manns et al., The acu-menTM: A new device for continuous renal replacement therapy in actue renal failure, Kidney International, 1998, pp. 268-74, vol. 54.

* cited by examiner

MULTI-PASS DIALYSIS

BACKGROUND

The field of the application is that of dialysis and renal failure therapy, using a renal failure therapy fluid, whether for hemodialysis or peritoneal dialysis. The invention provides an apparatus and a method for increasing the proportion of wastes from the patient before the renal failure therapy fluid is discarded.

A person's kidneys may fail, and the person may then require dialysis. In some situations, a person must be treated at a dialysis center, such as a hospital or a clinic. In other situations, if the person is able or has a caregiver, dialysis at home is a feasible treatment option. Dialysis may begin with peritoneal dialysis, as a first step, with no direct contact required with the person's blood. After a period of time, the person may require a more effective treatment, hemodialysis.

There are several problems and inconveniences associated with home dialysis. One of the problems is that once treatment begins, a person must continue treatment in order to live, and is thus tied to a bulky, heavy peritoneal dialysis machine or a hemodialysis machine. Another problem is that once home treatment begins, a person becomes accustomed to a particular dialysis machine. It is a burden and an inconvenience if the person has to shift from a peritoneal dialysis machine to an unfamiliar, hemodialysis machine as his or her health deteriorates and hemodialysis becomes necessary. Another disadvantage is that the person, or a caregiver, must handle many heavy bags of dialysis fluid on a daily basis.

Dialysis machines are typically not portable, and are designed for use in the home, as opposed to a design for transportability. Consider, for example, the Aksys PHD machine and the NxStage System One® machine. The AKSYS PHD hemodialysis machine, with markedly improved pre-treatment steps and set-up time, is more compatible with a home environment. However, it requires a water pre-treatment system in the home and may be larger and no more mobile than a conventional hemodialysis machine. The NxStage System One® machine is smaller than a conventional dialysis machine (about 70 lbs or 32 kg) and is thus somewhat portable. This machine does not require installation of a water treatment system in the patient's home and may be connected to a separate device that generate dialysis solution from tap water and concentrates. This separate device, the PureFlow SL, utilizes a replaceable cartridge that includes the necessary filters, deionizers, sorbents, and so forth, and requires attention during processing, in addition to servicing at least once per month for at least the sorbents, filters and deionizers. Alternatively, the machine may use pre-sterilized bags of dialysis solution, another disadvantage of home dialysis.

Another disadvantage is the volume of dialysis fluid used in treatment, whether for peritoneal dialysis or hemodialysis. In a typical treatment session for peritoneal dialysis (PD), about 10-15 liters of dialysis fluid are used. In a typical thrice-weekly hemodialysis therapy, more than about 90 liters of dialysis fluid are used per treatment session. In one example, a dialyzer may require a flow rate of about 500 ml/min for a three-to-four hour period, for a total of about 90-120 liters, about 24 to 32 gallons. This is clearly a large amount.

In home treatment, the patient, or a caregiver, must transport the dialysis fluid from a spare bedroom. Basement, garage, or large closet inside the home, and arrange the bags of fluid near the peritoneal dialysis or hemodialysis machine. Dialysis patients are typically older and in relatively poor health. A caregiver, who may be a spouse or relative of the patient, is also frequently elderly. These people may find burdensome the logistics of transporting, moving, and arranging heavy bags of dialysis fluid. If treatment is conducted three-times weekly, the burden is frequent. If treatment occurs daily, the bags of fluid must then be handled on a daily basis and the burden becomes very frequent.

It would be convenient if the patient were not tied to a large, bulky dialysis machine, and could use the same machine for both peritoneal dialysis and for hemodialysis. It would also be desirable to reduce the amount of dialysis fluid required for treatment, whether for peritoneal dialysis or hemodialysis.

SUMMARY

One embodiment is a dialysis system. The dialysis system includes a dialyzer having dialysis fluid inlet and outlet ports, a blood pump connected to the dialyzer for pumping blood from a patient, at least one drip chamber in series with the dialyzer, a first multi-position valve for connection between the patient and the blood pump, and a second multi-position valve for connection between the patient and the drip chamber, wherein the first valve and the second valve are capable of connection in a first position for the first valve to allow a flow of blood from the patient to the blood pump and the second valve to allow a flow of the blood from the drip chamber to the patient, and are capable of connection in a second position for the second valve to allow a flow of blood from the patient to the blood pump and the first valve to allow a flow of the blood from the drip chamber to the patient. The dialysis system also includes a source of fresh dialysis fluid in series with the dialysis fluid inlet port, a pump connected with the source of the fresh dialysis fluid, interconnecting lines between the patient and the valves for drawing blood from the patient and returning the blood to the patient, and a connection from the dialysis fluid outlet port to the dialysis fluid inlet port that allows recirculation of spent dialysate from the outlet port to the inlet port, and wherein a number of passes of spent dialysis fluid through the dialyzer is set by a ratio of a flow of spent dialysis fluid within the dialyzer to a flow of fresh dialysis fluid to the dialyzer.

Another embodiment is a dialysis system. The dialysis system includes a dialyzer having dialysis fluid inlet and outlet ports, a blood pump connected to the dialyzer for pumping blood from a patient, at least one drip chamber in series with the dialyzer, a source of fresh dialysis fluid in series with the dialysis fluid inlet port, a pump connected with the source of the fresh dialysis fluid, and at least one of a balance chamber or a flow channel between the dialysis fluid outlet port and the dialysis fluid inlet port for balancing a flow of fresh dialysis fluid and spent dialysis fluid to the dialysis fluid inlet port, and wherein a number of passes of spent dialysis fluid through the dialyzer is set by a ratio of a flow of spent dialysis fluid within the dialyzer to a flow of fresh dialysis fluid to the dialyzer.

Another embodiment is a method for conducting hemodialysis. The method includes a step of providing a hemodialysis system, the hemodialysis system comprising a blood pump, a dialyzer, a drip chamber, a source of fresh dialysis fluid, and a drain. The method also includes steps of providing access to and from blood vessels of the patient through valves connected to the blood pump and the drip chamber, circulating dialysis fluid from the source to the dialyzer, pumping blood from the patient and to the patient through the dialyzer, recirculating the used dialysis fluid to the dialyzer, wherein the used dialysis fluid optionally includes a proportion of fresh dialysis fluid, and draining the used dialysate fluid, wherein wastes from blood of the patient are transferred to the dialysis fluid in passing through the dialyzer.

Another embodiment is a method for conducting hemodialysis. The method includes a step of providing a hemodialysis system comprising a blood pump, a dialyzer, and a drip chamber. The method also includes steps of providing access to and from blood vessels of a patient, pumping blood from the patient through the dialyzer and returning the blood to the patient, circulating fresh dialysis fluid to the dialyzer, recirculating the used dialysis fluid to the dialyzer, wherein the used dialysis fluid optionally includes a proportion of fresh dialysis fluid, and draining the used dialysate fluid, wherein wastes from blood of the patient are transferred to the dialysis fluid in passing through the dialyzer.

Another embodiment is a dialysis system. The dialysis system includes a first dialysate pump connected to a source of fresh dialysis fluid, a dialysate warmer, a second dialysate pump for pumping used dialysate fluid from a peritoneum of a patient, a balancing system operably connected to the source of fresh dialysis fluid and to the peritoneum of the patient for balancing and mixing the flows of fresh dialysis fluid and spent dialysis fluid to and from the peritoneum of the patient. The system optionally includes a filter, such as a sorbent bed, for filtering the used dialysate before it is returned to the peritoneum of the patient, and valves and interconnecting lines, the valves and interconnecting lines configured for setting a ratio of fresh dialysis fluid to used dialysis fluid for pumping to the peritoneum of the patient, and for admitting fresh dialysis fluid at a known rate and draining used dialysis fluid at the same known rate.

Another embodiment is a method for conducting peritoneal dialysis. The method includes a step of providing a peritoneal dialysis system, the peritoneal dialysis system comprising a fresh dialysis pump, a used dialysis pump, a source of fresh dialysis fluid, a fluid mixing system, and a series of interconnecting lines and valves. The method also includes steps of providing access to and from a peritoneum of the patient through the valves, circulating dialysis fluid from the source to the peritoneum, pumping fresh dialysis fluid to the peritoneum, recirculating used dialysis fluid to the fluid mixing system, wherein the used dialysis fluid includes a proportion of fresh dialysis fluid. The method also includes steps of recirculating the used dialysis fluid to the peritoneum of the patient, and draining the used dialysate fluid, wherein wastes from the patient are transferred to the dialysis fluid in passing through the peritoneum. The quantity of used dialysate drained during each cycle equals the quantity of fresh dialysate admitted during each cycle.

Additional features and advantages are described herein, and will be apparent from, the following Detailed Description and the figures.

DETAILED DESCRIPTION

Figure 1:
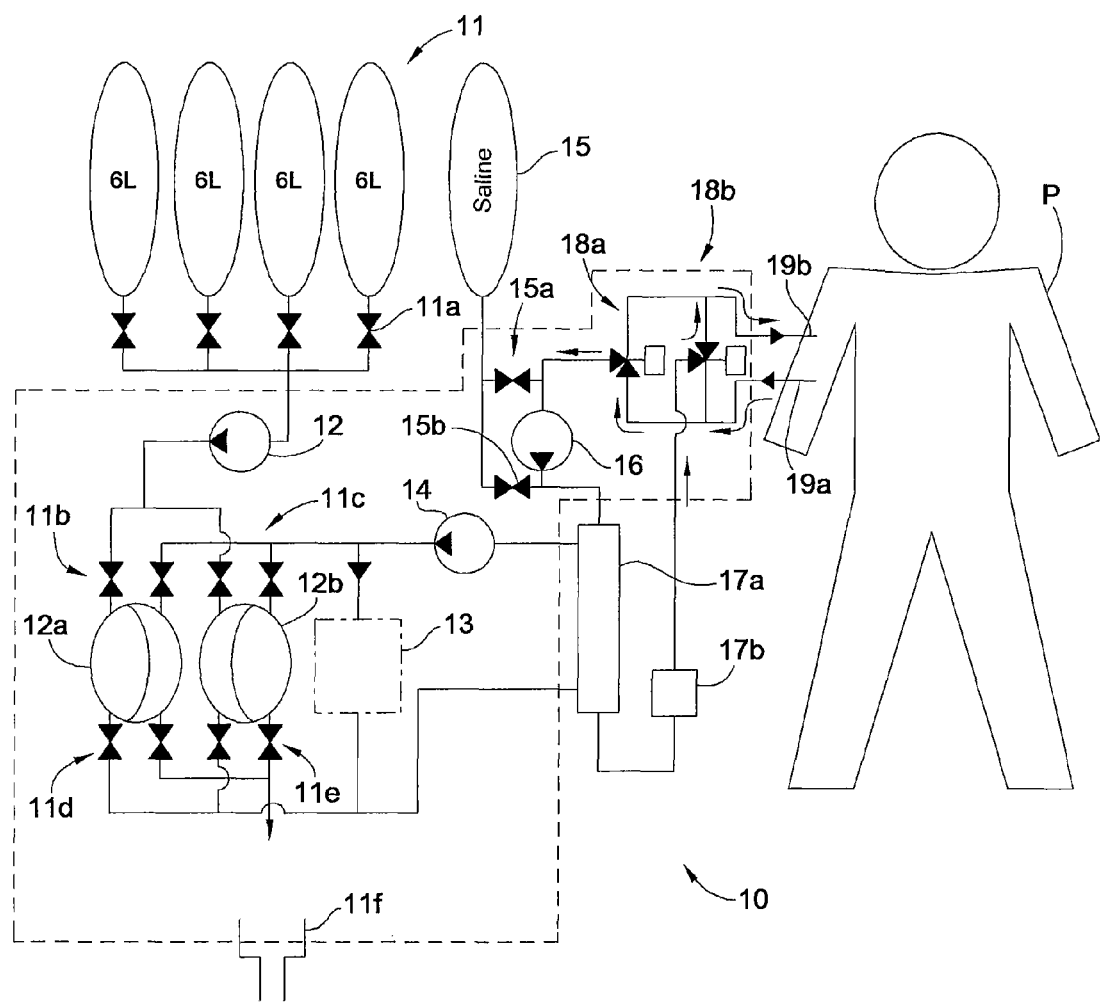
FIGS. 1-2 are diagrams of a system for using renal failure therapy fluid several times in a home hemodialysis setting with balance chambers and using standard arterial and venous needles.

Conventional dialysis treatment does not use the dialysis fluid to its greatest advantage because the fluid is not saturated with wastes from the blood of the patient over all the range of molecular weights that are present in the blood of the patient. The cost of treatment would be lower if the used dialysis fluid contained the maximum amount possible of one or more toxins from the patient's blood, as shown in Table 1. Table 1 is taken from Kidney International, vol. 58, Suppl. 76 (2000), pp. S-47 to S-59, *The Removal of Uremic Toxins*, by A Dhondt, et al., which is hereby incorporated by reference in its entirety. The article indicates that dialysis, like natural kidney function, easily removes small, water-soluble molecules, such as urea. Other waste molecules may be more difficult, especially those that are marked with a + in the table, such as protein-bound molecules. If the dialysate fluid were concentrated with at least one of the toxins from the patient's blood, less fluid would be needed, and the patient would not have to store, carry and otherwise handle so much dialysis fluid. Urea is easily removed from the blood by dialysis.

TABLE 1

Uremic toxins: Characteristics and dialytic removal

| Type | Hydrophobic | Protein bound | Dialytic removal parallel with urea |
|---|---|---|---|
| Small water-soluble molecules | | | |
| Guanidines | − | − | − |
| Purines | − | − | ± |
| Oxalate | − | − | + |
| Phosphorus | − | − | − |
| Urea | − | − | |
| Middle molecules | | | |
| Cystatin C, Clara cell protein, leptin | − | − | − |
| Advanced glycosylation end products | ± | ± | − |
| Oxidation products | ± | ± | − |
| Peptides (β-endorphin, methionine-enkephalin, β-lipotropin, GIP I, GIP II, DIP, adrenomedullin) | − | − | − |
| β$_2$-microglobulin | − | − | − |
| Parathyroid hormone | − | − | − |
| Protein bound compounds | | | |
| Indoles (indoxyl sulfate) | + | + | − |
| Carboxy-methyl-propyl-furanpropionic acid (CMPF) | + | + | − |
| Hippuric acid | ± | + | − |
| P-cresol | + | + | − |
| Polyamines (spermine, spermidine, putrescine, cadaverine) | + | + | − |

The cost of the therapy would also be lower, because less dialysate fluid would need to be purchased. A higher concentration of waste is generated in the dialysis fluid by passing the dialysis fluid through the dialyzer multiple times, that is, in multiple passes. This is accomplished, for example, by slowing the rate of blood flow through the dialyzer and using pumps and valves to recycle a portion of the dialysis fluid until it is saturated with at least one waste product from the person's blood, such as beta-2-microglobulin. The slower pumping rates also reduce the noise generated by the dialysis system operation, making is more suitable for performing a night-based therapy. If the technique is used for peritoneal dialysis, the dialysis fluid is passed through the patient's peritoneal cavity more than once. There are many techniques for determining the concentration of any particular toxin or by-product in the blood or in the used dialysate. See e.g., U.S. Pat. No. 5,518,623, which is hereby incorporated by reference in its entirety and relied on, outlining techniques for calculating concentrations and clearances of urea, and noting that similar techniques may be used for a number of other constituents of spent dialysis fluid, such as beta-2-microglobulin, creatinine, and so forth. The concentrations of other toxins, noted above in Table 1, may also be calculated and dialyzer efficiency determined.

Figure 2:
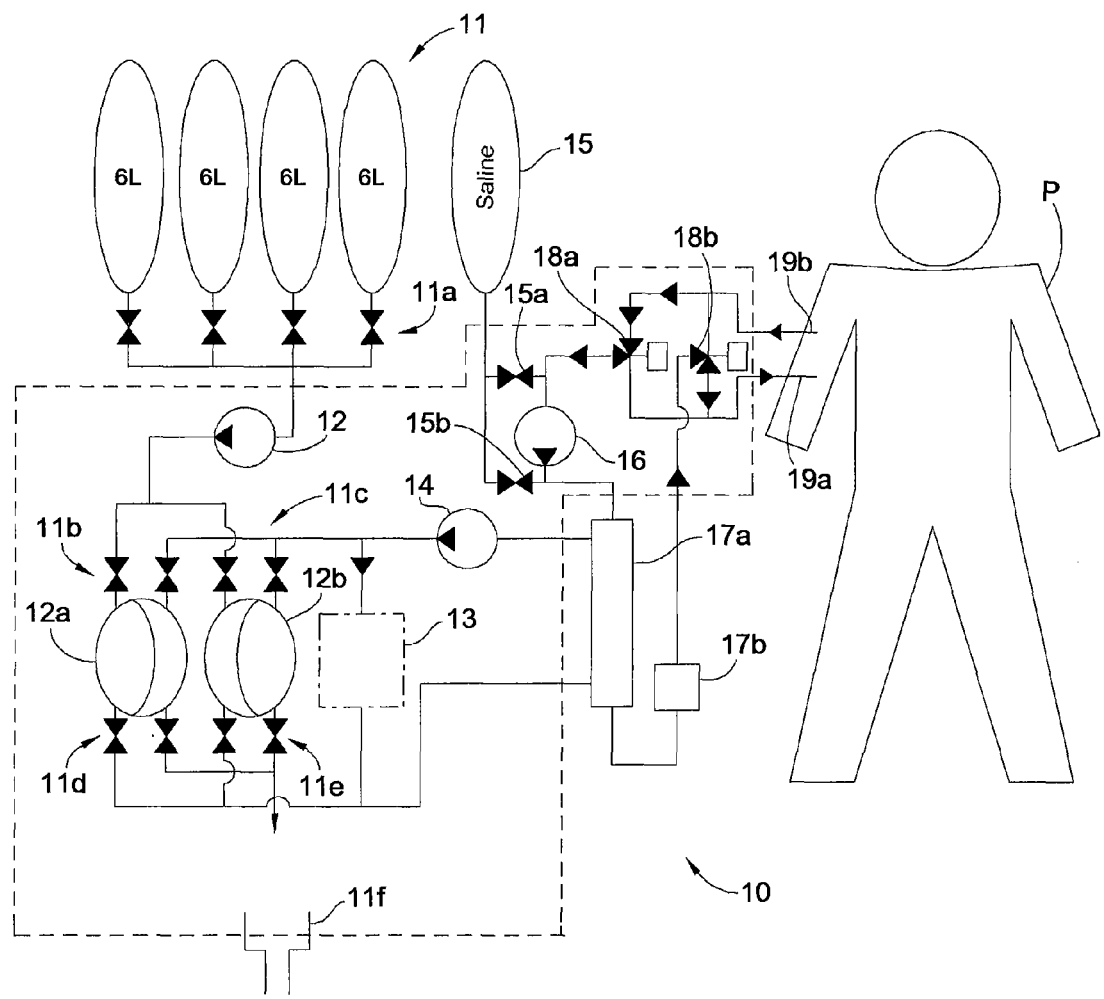

A first embodiment of a multiple-pass hemodialysis system is depicted in FIGS. 1-2. In FIG. 1, a multi-pass hemodialysis system 10 is connected to a patient P for hemodialysis. The hemodialysis may take place at home, i.e., home hemodialysis, or it may take place in a clinical setting, e.g., a hospital or a clinic. A plurality of containers 11 of dialysis fluid is connected via valves 11a to a pump 12. Pump 12 may be any suitable pump, such as a peristaltic pump or a diaphragm pump. Under control of a system controller, not shown, fresh dialysis fluid is admitted through valves 11b to balance chambers 12a, 12b, and flows through valves 11d to a dialyzer 17a. The system may also include a container 15 of sterile saline through a valve 15a upstream or a valve 15b downstream of the blood pump 16. Saline or fresh dialysate in container 15 may be administered as a bolus to the patient if needed.

Dialyzer 17a is connected to the patient P through a blood pump 16 on the arterial side, and through a blood drip 17b on the venous or return side. The patient is connected through needles 19a, 19b, which may be standard arterial and venous needles, or may be single-needle embodiments, each needle suitable for alternate withdrawal and return of blood from the patient, but not for simultaneous withdrawal and removal. By using only single needle blood access, the need for an access disconnect system is obviated. Alternately, if standard arterial and venous access needles are used, an access disconnect system should be used, to safeguard patient safety and prevent. Access disconnect systems are disclosed in several patents and patent applications assigned to the assignee of the present patent document. See, e.g., U.S. Pat. Nos. 7,022,098, 7,052,480, and 7,138,088, each of which is hereby incorporated by reference in its entirety.

It is understood that a heater may be used to warm the dialysis fluid so that the blood of the patient is not cooled. In embodiments for peritoneal dialysis, it is also important that the dialysis fluid be warmed to avoid shock to the patient when the patient is treated with dialysis fluid. The heater may be placed before or after the cassette or disposable used in therapy. In the systems and methods described here, there may be an additional auxiliary heater for the used dialysate intended for re-use, such as after the filter, but in any case before cool, re-used fluid enters the peritoneum or the dialyzer.

In one embodiment, needles 19a, 19b connect the patient to the dialyzer through valves 18a, 18b. The valves may be three-way cassette-based, three-way pilot-operated diaphragm valves, described in more detail below in FIGS. 11-12, although other suitable sterile fluid pathway valves may be used. In one application, valve 18a is open to the dialyzer 17a and is also open to lower needle 19a, thus connecting the lower needle 19a for arterial access. Valve 18a in this application is turned so that it does not connect to upper needle 19b. At the same time, upper needle 19b is used for venous access, and valve 18b is open to needle 19b and to the line connected to the blood drip chamber 17b, for returning blood from the dialyzer. Of course, in this application, valve 18b is not open to lower (arterial) needle 19a. In performing hemodialysis in this "double" single needle technique, the valves are switched periodically and the flow of blood reversed. Using this technique, if one of the needles becomes dislodged, blood loss is kept to a minimum, because the air sensors (not pictured) typically provided in the hemodialysis machine will detect air from whichever needle is on the arterial side. The valves are switched periodically, for example, every 15 to 20 seconds.

To recycle dialysis fluid, a portion of the spent or used fluid from dialyzer 17a is then pumped by a second pump 14 through a carbon filter 13, which removes at least a portion of the creatinine and beta-2-microglobulin from the dialysis fluid, but typically does not remove other wastes, such as urea. This portion of the spent dialysis fluid is recycled into the dialyzer for further a second or subsequent pass. One or two downstream connected valves 11c may be opened the desired amount to admit spent dialysis fluid to one or the other of the balance chambers. Those having skill in dialysis arts will recognize that the flows of fluid on either side of a balance chamber should be balanced. Thus, the rate of fresh dialysis fluid admitted from the dialysis source containers 11 will match the rate of admission of spent dialysis fluid on the other side of the balance chambers. The remainder of the spent dialysis fluid is recycled, in this example filtered and sent back to the dialyzer. The spent dialysis fluid admitted to the balance chambers 12a, 12b is discharged through valves 11e to drain 11f, while the fresh is sent to the dialyzer.

In one example, if a flow of 200 ml/min to the dialyzer is desired, and flow from the source of fresh dialysis fluid is 50 ml/min, then 50 ml/min is also sent to the drain. Mixing will occur during the process, but in this design, the dialysis fluid will pass through the dialyzer four times, on average, before it is discharged to drain 11d, that is, this will be a four-pass system. Other ratios may be used, such as a two-pass system, a three-pass system, and so forth. On each pass through the dialyzer, the dialysis fluid absorbs more toxins from the patient's blood, until, of course, the particular toxin is no longer soluble in the dialysis fluid. Some toxins, as noted, may be removed by a carbon or other filter, but this will not suffice for urea and certain other wastes.

It will be recognized by those having skill in dialysis arts that a dialysis machine can perform many of the pumping and detection functions described above with respect to FIG. 1, and also with respect to the descriptions below for the remaining figures. The valving and flow balancing functions may be accomplished with a disposable cassette used in the dialysis machine. In the figures below, including FIGS. 1-2, the disposable portion of the dialysis machine includes most of the components depicted, such as the valves and the pumps, but does not include the dialyzer, the blood trap, and the containers of fluid or saline. In FIGS. 1-2, the disposable portion of the dialysis machine is contained within dashed lines. The burden on the patient is lessened if the valves reside within the cassette, rather than near the access points, e.g., an arteriovenous fistula, on the patient. It should also be understood that the lines connecting the patient to the machine are longer than depicted, and may be from 1 to 10 feet long, for example.

The dialysis machine is typically not in intimate contact with dialysis fluids, such as the dialysis fluid itself or with blood of the patient, while the cassette, and in hemodialysis, the dialyzer, are in such intimate contact. Controlling costs for the dialysis patient suggests putting as much functionality as possible into the dialysis machine, which is reused continuously, while trying to minimize the functions, and thus the costs, associated with the disposable items, including the disposable cassette and the dialysis fluid. Hemodialysis cassettes may include the dialyzer, which also intimately contacts the blood of the patient as well as the dialysis fluid. Of course, another way to minimize the costs and to keep the patient as comfortable is to be able to use the same dialysis machine for peritoneal dialysis as for hemodialysis.

It may be useful to analyze the used dialysate fluid to determine whether it is saturated in one of more of the important species or toxins intended to be removed from the blood or peritoneum of the patient. The measurements must be very fast, virtually on-line, in order to determine when the saturation has occurred. For example, at least urea, glucose, and phosphate may be determined from on-line measurements using infrared transmission spectroscopy. See, e.g., Determination of Urea, Glucose, and Phosphate in Dialysate with Fourier Transform Infrared Spectroscopy, P. S. Jensen et al., Spectrochim Acta A Mol. Biomol. Spectrose., 60 (4), pp. 899-905, March 2004. The near-infrared range and other techniques may also be used to detect at least urea. See *Online Monitoring of Urea Concentration in Dialysate with Dual-Beam Fourier-transform Near-Infrared Spectroscopy*, P. S. Jensen et al., J. Biomed. Opt., 9 (3) pp. 553-57, May-June 2004. See also, *Near-Infrared Spectroscopy for Measuring Urea in Hemodialysis Fluids*, C. V. Eddy et al., Clinical Chemistry, 47 (7), 1279-86 (2001). Each of these three papers is hereby incorporated by reference in its entirety, as though each page and figure were set forth herein.

Other techniques may use previously-developed relationships between the concentrations of one impurity or toxin and another, or may use known relationships of how many recycles are required or permissible for removal of a given substance. In yet other embodiments, the depletion of a substance in the dialysis fluid, such as glucose, may be used to determine when a used dialysis fluid should be discarded.

FIG. 2 depicts the apparatus of FIG. 1 with the valves reversed, and the functions of the needles also reversed. In FIG. 2, upper needle 19*b* now supplies arterial access, while lower needle 19*c* provides venous return access. The needles 19*a*, 19*b* may reside in an arteriovenous fistula so that their functions can be easily reversed. Alternately, the patient blood lines may connect directly to a catheter that is compatible with reversible blood flows. Valve 18*a* now connects upper needle 19*b* and the dialyzer blood pump, and access is closed to the lower needle 19*a*. Valve 18*b* is closed to upper needle 19*b* and provides a pathway from the blood drip 17*b* to lower needle 19*a*.

Figure 3:
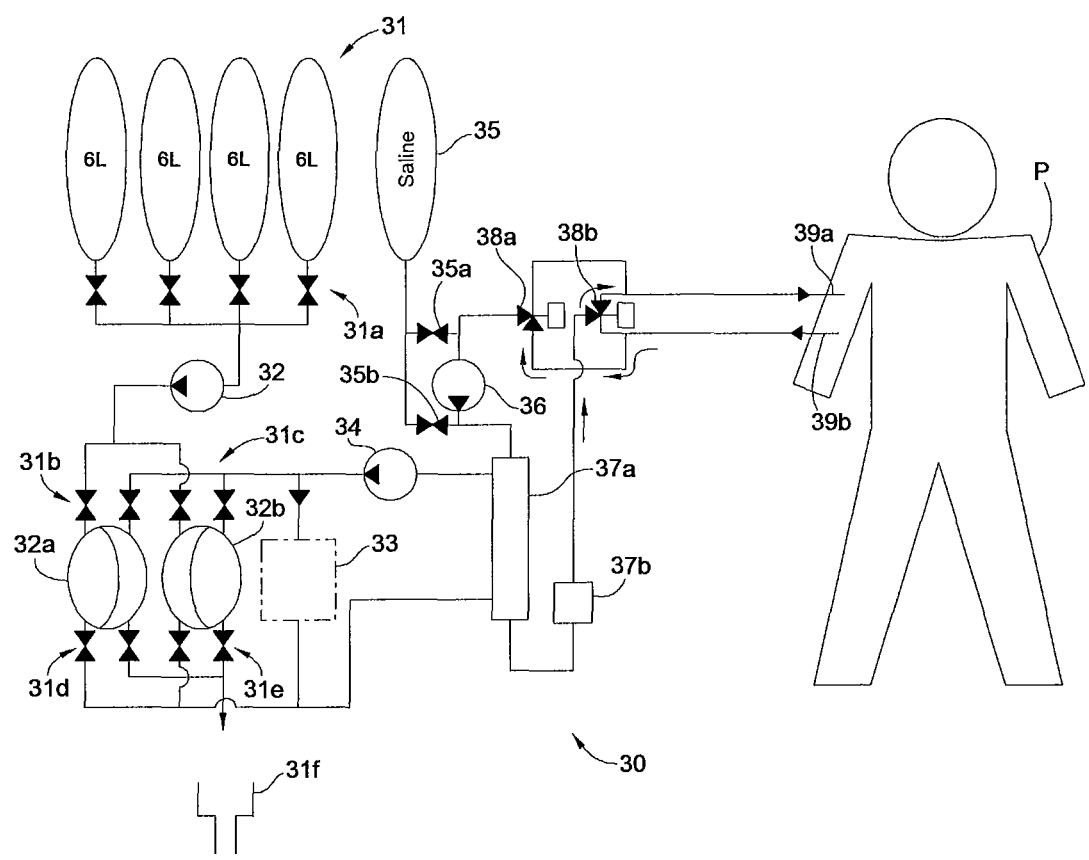
FIGS. 3-4 are diagrams of a hemodialysis system using renal failure therapy fluid in a single needle application.
Figure 4:
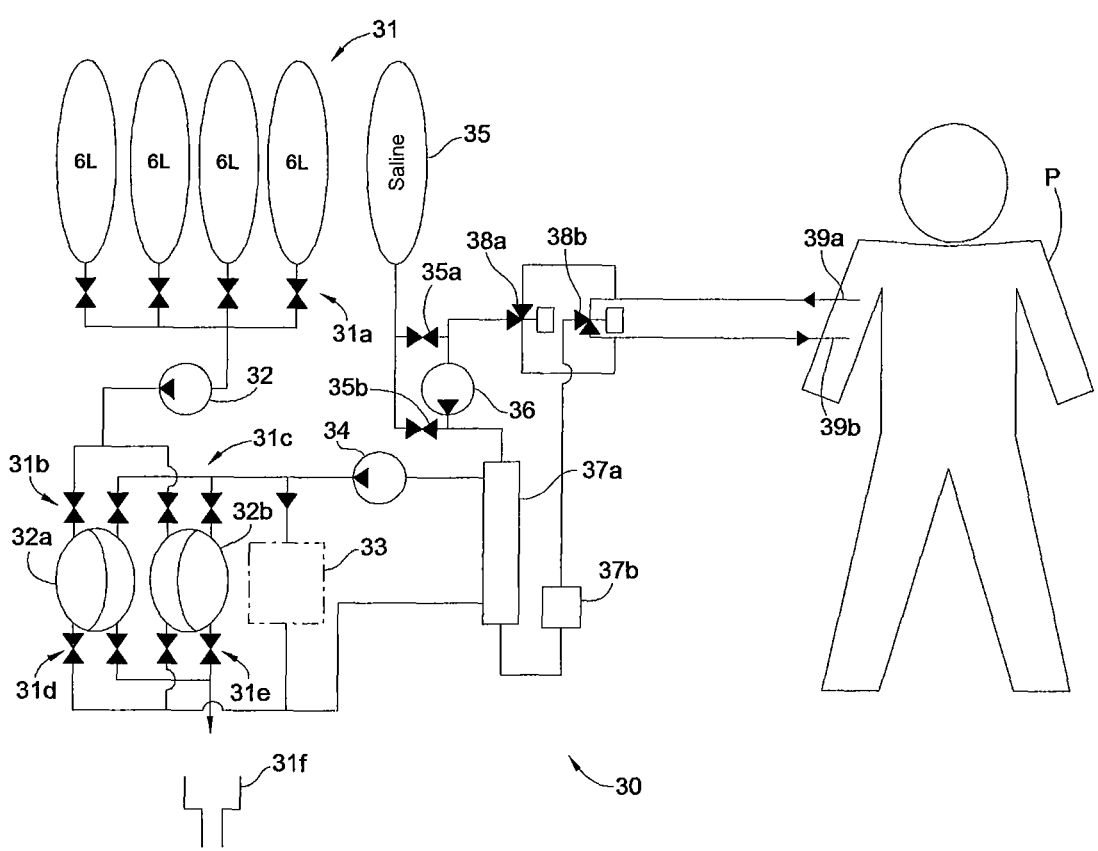

FIGS. 3-4 are similar to FIGS. 1-2, with a change in the connections between the valves, and also suggesting that the lines connecting the patient P to the hemodialysis machine may be several feet long, longer than the lines depicted in FIGS. 1-2. Hemodialysis machine 30 is connected to a patient P for a hemodialysis treatment. The machine connects a plurality of containers 31 of dialysis fluid through a first set of valves 31*a* to a fresh dialysis fluid pump 32. The machine also includes a container 35 of saline which is connected via valve 35*a* or 35*b* to blood pump 36. The fresh dialysis fluid pump 32 connects via a second series of valves 31*b* to balancing chambers 32*a*, 32*b*, while the opposite sides of the balancing chambers connect through valves 31*c* to admit used or spent dialysis fluid. The discharge from the "fresh" side of the balancing chambers connects through another series of valves 31*d* to the dialyzer 37*a* or, on the used or spent side, through valves 31*e* to the drain 31*f*. Note that the balancing chambers function almost exactly as in a standard dialysis machine, balancing the flow of fresh and spent dialysis fluid. Pump 34 recycles the used dialysis fluid to filter 33 or to the balancing chambers through valves 31*c*, where the fluid is sent to drain 31*f* through valves 31*e*.

Blood valves 38*a*, 38*b* are configured differently from the valves in the previous embodiments. Valves 38*a*, 38*b* are both connected in parallel to both valves. The valves are then operated by the controller so that they still function in a single-needle mode, with one providing arterial access and the other providing venous access. Thus, in FIG. 3, valve 38*b* is closed to lower needle 39*b*, and blood from the lower needle thus flows to valve 38*a* and then to the dialyzer. Valve 38*a* is closed to needle 39*a*. Valve 38*b* is open to upper needle 39*a* and also to drip chamber 37*b*, and thus provides a return path for the blood. In FIG. 4, valves 38*a*, 38*b* are reversed, and now upper needle 39*a* provides arterial access through valve 38*a*, while valve 38*b* is closed to the upper needle. Lower needle 39*b* provides a return through valve 38*b*, which is open to the return line from drip chamber 37*b*.

Figure 5:
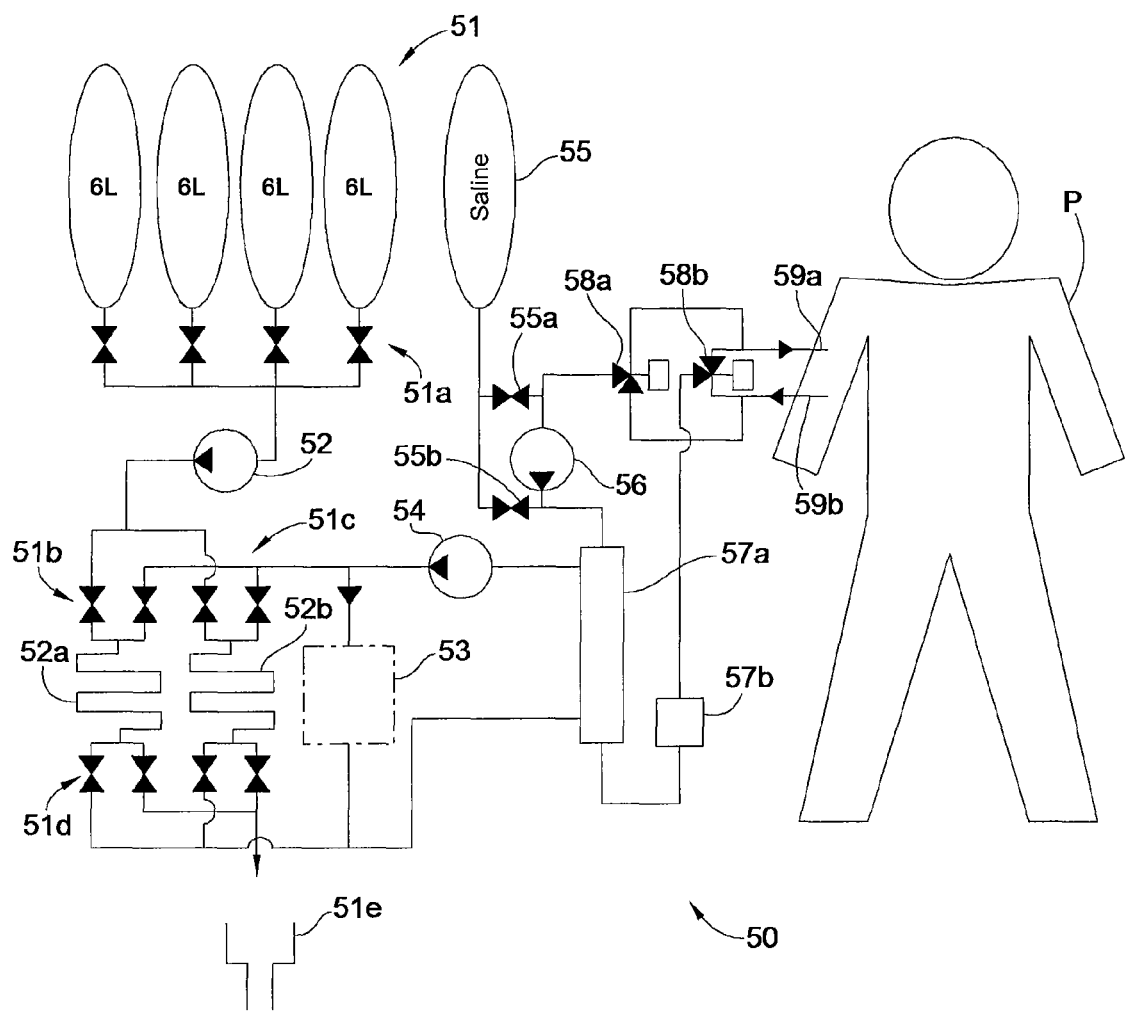
FIGS. 5-6 are diagrams of a single-needle hemodialysis system with flow channels rather than balance chambers.
Figure 6:
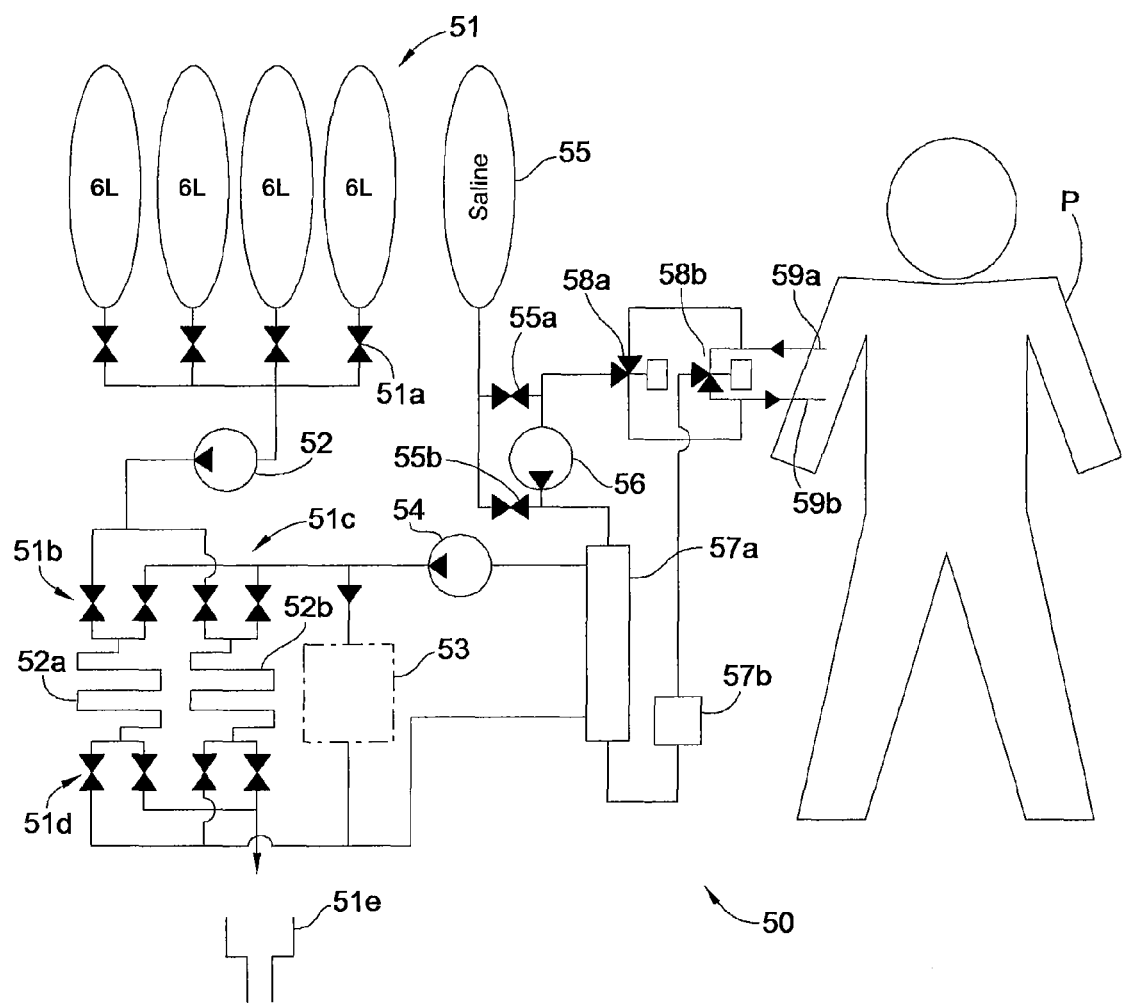

Another embodiment is depicted in FIGS. 5-6, which uses flow channels to balance the inflow of fresh dialysate with the outflow of spent dialysate while recirculating the mixture to the dialyzer so that at least a part of the dialysate has at least two passes. In FIG. 5 of this embodiment, hemodialysis system 50 connects to patient P for a hemodialysis treatment. The hemodialysis system connects to sources of dialysis fluid, such as containers 51 through a series of valves 51*a* and through fresh dialysis fluid pump 52. A separate container 55 of saline may be provided to the patient for administration of a bolus of saline through upstream valve 55*a* or downstream valve 55*b*. Three-way valves 58*a*, 58*b* are connected as previously described. In FIG. 5, valve 58*a* is open to lower needle 59*b* to provide blood to blood pump 56 and to dialyzer 57*a*. For the return, valve 58*b* is open to the line from the drip chamber 57*b* to return blood via upper needle 59*a*. Note that valve 58*a* is closed to the alternate line from needle 59*a* to the valve.

This embodiment uses flow channels, one example of which is a serpentine pattern that starts in the bottom of a cassette and works its way towards the top so that air will not become trapped in the flow channel. This serpentine pattern also provides long paths with increased volume in the flow channels for mixing the fresh dialysate with the used dialysate before the next pass. The flow channels can result in a simplified, less expensive, more compact disposable and the increased volume results in improved volumetric flow balancing accuracy. The larger volume of the flow channels reduce the effect of the fixed volumetric error that results from switching of the valve positions. As the flow volume increases, the effect of a small relative error decreases. Spent and fresh dialysate will mix on each end of the volumes of fluid when the flow channels switch. In a single pass mode, this could waste as much as 20% of the fresh dialysate. In a multiple pass, none is wasted.

Fresh dialysis pump 52 connects through a first series 51*b* of valves to parallel flow channels 52*a*, 52*b*. The portion of the used dialysis fluid not admitted to the flow chambers valves 51*c* flows through filter 53, which may be a carbon filter or may be another type of filter. The portion of used dialysate passing through the filter is routed back to the dialyzer 57*a* for an additional pass. The outlet of the flow channels is directed through another series 51*d* of valves to either drain 51*e* or to dialyzer 57*a*. Thus, used dialysate fluid may be routed through the filter or through the flow channels. Once through the flow channels, it may be returned to the dialyzer for reuse or may be directed to the drain. This system has an additional degree of freedom not present in systems using diaphragm or other balancing systems, with better mixing of the used dialysate with the fresh dialysate. This system also has the freedom to send a different proportion of the spent dialysate through the filter rather than requiring all the re-used dialysate to pass through filter 53.

The ratio of dialysate recycle flow to the flow to drain is a measure of the number of passes through the dialyzer. Thus, if 200 ml/min of mixed fresh and spent dialysate is routed to the dialyzer, and 50 ml/min are routed to the drain, the ratio is 4/1, and on average, there will be 4 passes of dialysate routed through the dialyzer before it is discarded. In this example, 50 ml/min of fresh dialysate should also be provided through the flow channels to make up for the discarded or spent dialysis fluid. It should also be noted that the contact time with the blood in the dialyzer is desirably increased to allow for extra diffusion of the impurities in the blood across the dialyzer membrane. Thus, if a system is used with a two-pass ratio, the contact time with the blood, i.e., the blood flow rate, should be proportionately increased. This means that the flow rate of the blood, in this example, may be halved. If other flow or bypass ratios are used, the flow of blood may also proportionately decreased, and contact time in the dialyzer proportionately increased.

There are other degrees of freedom also. For example, if it is desired to use only fresh dialysate, the spent dialysate may be routed through flow channel 52b and then to the drain, without routing through the filter or through the other flow channel 52a. Of course, the flow rate of fresh dialysate in should match the rate of spent dialysate routed to the drain or other disposal. FIG. 6 is very similar to that of FIG. 5, but with valves 58a, 58b reversed, so that upper needle 59a now provides arterial access through valve 58a to pump 56 and the dialyzer, and lower needle 59b providing a return through valve 58b and drip chamber 57b. It will be recognized that these multi-pass techniques may also be applied to peritoneal dialysis.

Figure 7:
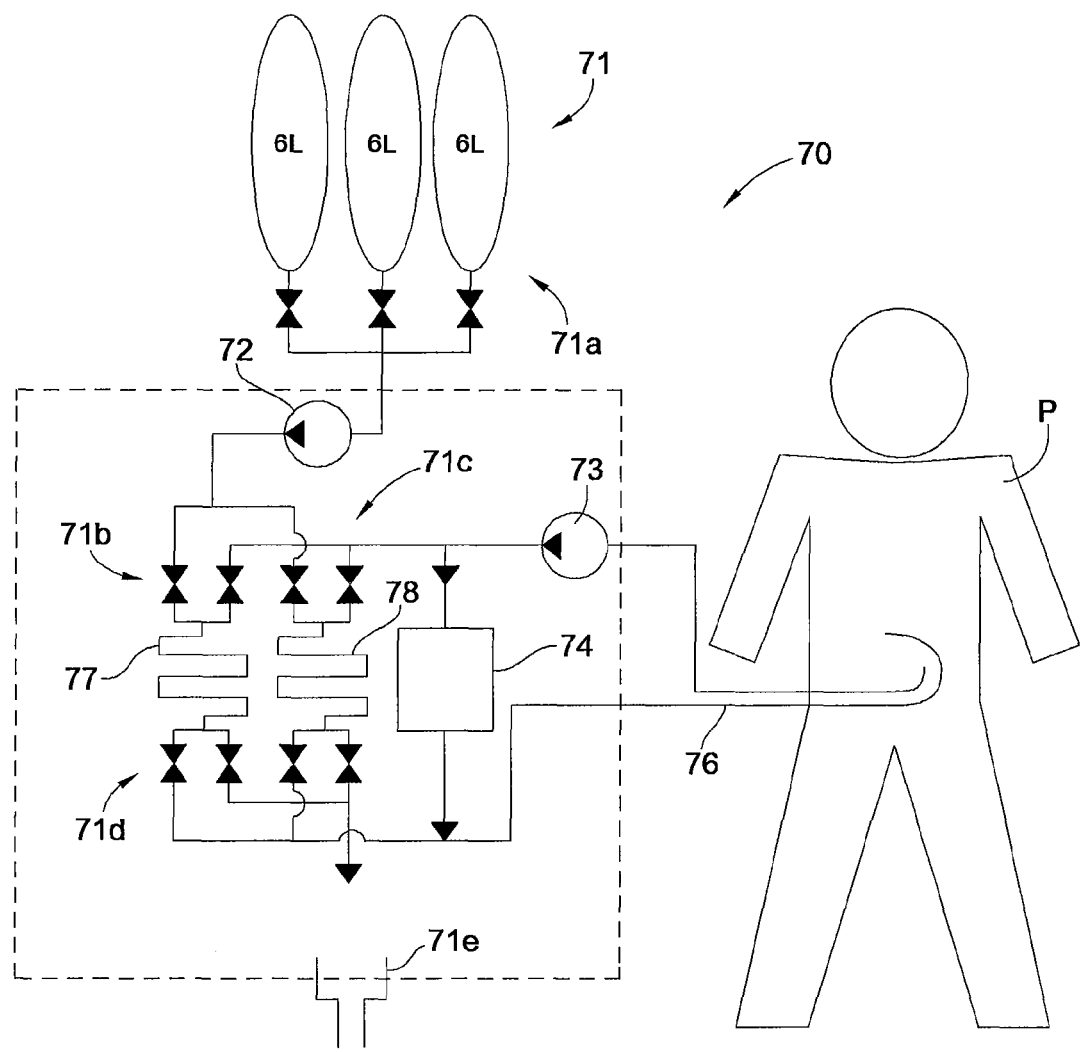
FIGS. 7-8 are diagrams of a peritoneal dialysis systems using flow channels for balancing dialysate flow.
Figure 8:
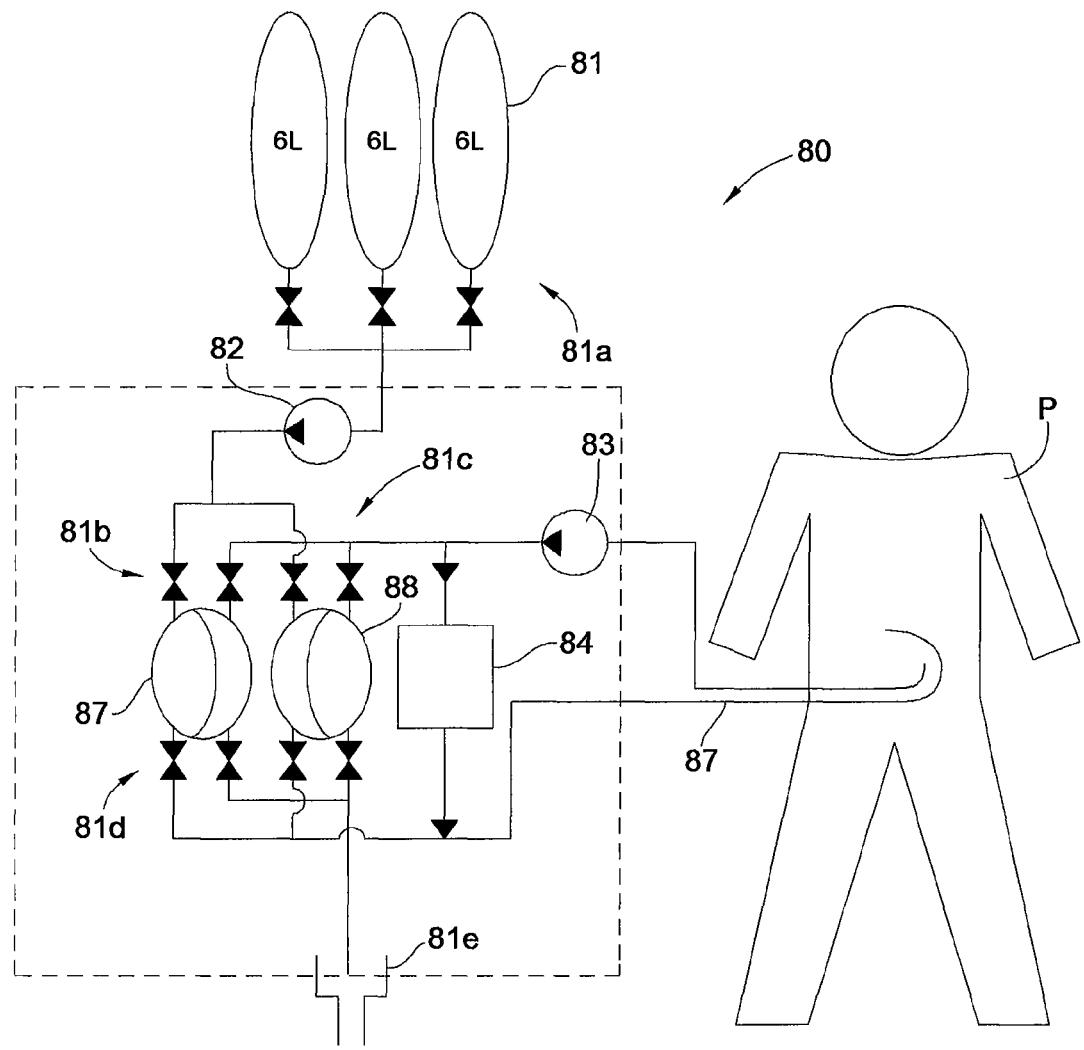

Accordingly, FIGS. 7-8 depict multi-pass dialysis machines that may also be used for peritoneal dialysis. FIG. 7 depicts a dialysis machine which is very similar to that depicted in FIGS. 5-6, except that instead of a dialyzer, the dialysis fluid is routed to a dual lumen peritoneal dialysis catheter which has been implanted within the patient P. Thus, the same dialysis machine, but with a different disposable, may be used for peritoneal dialysis as well as hemodialysis. In FIG. 7, peritoneal dialysis machine 70 with a cassette suitable for peritoneal dialysis contained within the dashed line, is connected to three containers 71 of dialysis fluid, which may be the same type of dialysis fluid or may be different. The containers are connected through a first series 71a of valves and a pump 72, which may be a peristaltic pump or may a different type of pump, such as a diaphragm pump. Other embodiments may use pumps that are not part of the disposable.

Pump 72 pumps fresh dialysate fluid through a second series 71b of valves, to flow channels 77, 78, which are also connected through a third series 71c of valves, which control flow of used or spent dialysis fluid from the outflow lumen of catheter 76. The fresh and spent dialysis fluid may mix within the flow channels, and their outlets are controlled by a fourth series 71d of valves, which direct the flow to drain 71e or back to the inflow lumen of catheter 76. Dialysis fluid is pumped into the patient where it remains for several hours to absorb toxins. When withdrawal is indicated, the catheter is connected to the dialysis machine, to pump 73, which may be a peristaltic pump or may be different type of pump, such as a diaphragm pump. The flow from pump 73 is directed through filter 74, which may be a carbon filter or may be a different type of filter.

As noted above for hemodialysis, the spent dialysis fluid may then be reused within the patient, or a part of the fluid may be sent to drain through valves 71, flow channel 77, 78, or both, and appropriate valves from the fourth series 71d. Fresh dialysis fluid may be admitted through valves 71b to either of the flow channels and mixed with spent dialysate, with an equal volume of spent or used dialysate then channeled to the drain 71c. It will be recognized that for the first fill, all fresh dialysis fluid is used, and for a final drain, all used or spent dialysis fluid is routed to drain. The volume of fluid removed from the patient may increase due to the toxins absorbed from the patient, and this increase in volume should be kept in mind for calculations of volume for discharged, spent, and fresh dialysis fluid volumes. The increase in volume typically ranges from 5-15% of the fill volume.

Another dialysis machine suitable for both peritoneal dialysis and hemodialysis is depicted in FIG. 8. The dialysis machine 80 is connected to patient P for dialysis. Dialysis machine 80 includes a cassette (within the dashed lines) suitable for peritoneal dialysis rather than hemodialysis, and is very similar to the machine depicted in FIG. 7, but with balance chambers 87, 88 rather than flow channels. Other embodiments may use pumps that are not part of the disposable. Dialysis machine 80 connects three containers 81 of dialysis fluid through a first series 81a of valves to a first pump 82, which may be a peristaltic pump or may be another kind of pump. Pump 82 then pumps fresh dialysis fluid through a second series 81b of valves to one or both of balancing chambers 87, 88, which also connect through a third series 81c of valves to pump 83. Pump 83 pumps used or spent dialysis fluid from the outflow lumen of catheter 87. The used or spent dialysis fluid may be routed through filter 84, where some of the toxins are removed before the used or spent dialysis fluid is rerouted to the patient's peritoneal cavity. Some or all of the used dialysis fluid may instead be routed to the balance chambers 87, 88 for disposal to the drain 81e. Note that balance chambers do not mix the fresh with the spent dialysate, in any rate, there is no thorough, intentional mixing. The amount of fresh dialysis fluid admitted with equal the spent fluid discharged if balance chambers are used.

Figure 9:
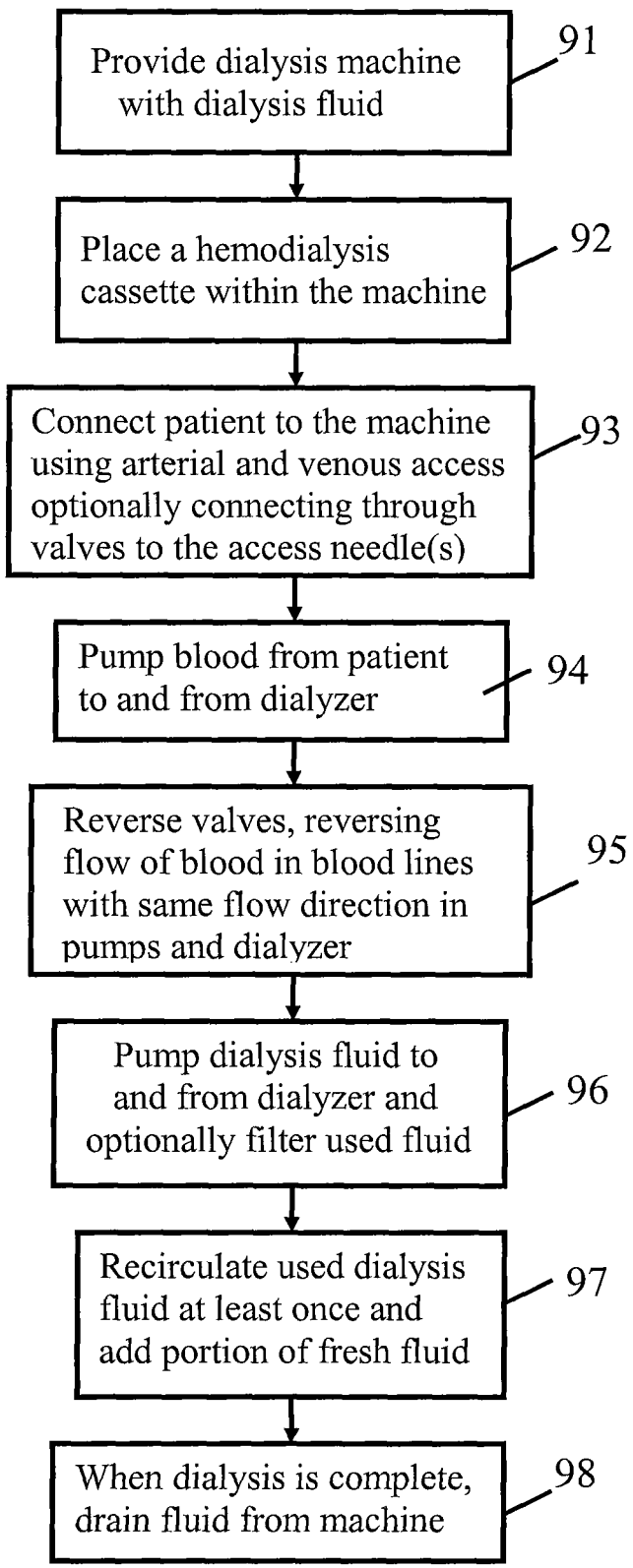
FIGS. 9-10 are flowcharts depicting method embodiments.
Figure 10:
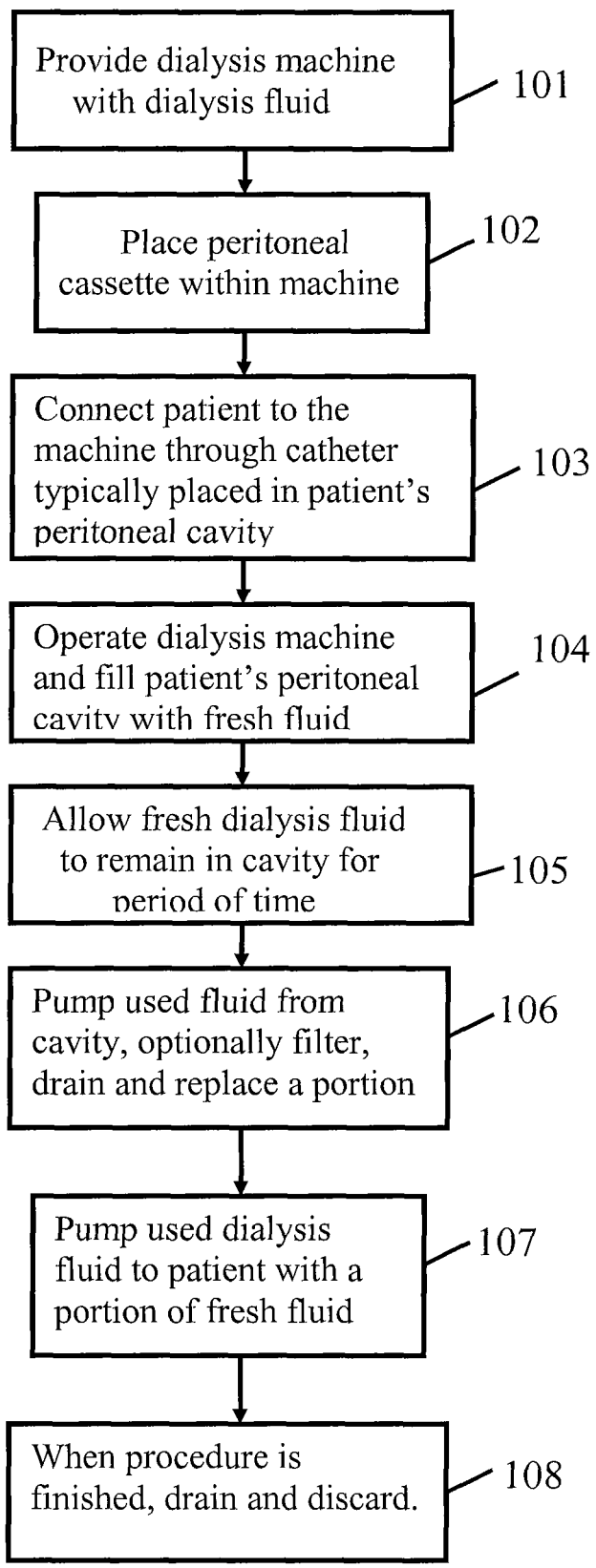

The methods of use for dialysis are presented in flow charts depicting steps of the process, as shown in FIG. 9-10. FIG. 9 is a flowchart depicting steps of using a dialysis machine in a multi-pass process for hemodialysis. The first step 91 is to provide a dialysis machine and a supply of fresh dialysis fluid. A cassette suitable for hemodialysis in then placed 92 into the machine. Those having skill in the art will recognize that a hemodialysis machine, or a peritoneal dialysis machine, have many components in common, and that the same machine, with a suitable cassette, may be used for both hemodialysis, as shown in FIG. 9, and for peritoneal dialysis, as shown in FIG. 10. These parts may include pumps, connections for the containers of dialysis fluid or saline, interfaces for the cassettes, controls and software, and so forth. The cassette typically includes the flow passages and valves, as depicted in the figures above. A hemodialysis cassette also typically includes a dialyzer, and thus is not suitable for peritoneal dialysis, while a peritoneal cassette typically does not include a dialyzer and thus is not suitable for hemodialysis.

The patient is then connected 93 to the machine using arterial and venous access. The access may be provided through standard venous and arterial needles, or through the valved needle connections described above. During hemodialysis, blood is pumped 94 to the dialyzer and back to the patient. In multi-pass hemodialysis, the flow of blood is slowed and is also periodically reversed 95, by reversing the valve positions as described above. On the other side of the dialyzer, dialysis fluid is pumped 96 to and from the dialyzer, at least a portion of the fluid filtered as desired. The dialysis fluid is recirculated at least once 97, for a two-pass process, and a portion of fresh fluid is added to make up for a portion of the used or spent dialysate that is drained or discarded. When dialysis is complete, the remainder of the spent dialysate fluid is drained 98 from the machine.

Another embodiment is a process for using the dialysis machine for peritoneal dialysis, as depicted in FIG. 10. A first step 101 is to provide the dialysis machine with a supply of dialysis fluid. A suitable peritoneal cassette 102 is placed into the machine, and suitable connections and interfaces are made to the pumps and controls of the dialysis machine with the sensors and surfaces of the cassette. The patient is then connected 103 to the machine through a catheter that is implanted within the peritoneal cavity of the patient. The catheter is typically a two-lumen catheter, for simultaneous filling and withdrawal of the liquid, but other catheters may be used. The dialysis machine is then operated 104 and the peritoneal cavity of the patient is first filled with fresh dialysis fluid. The fresh dialysis fluid is allowed to remain 105 within the peritoneal cavity for a period of time, typically several hours.

The used dialysis fluid is then pumped 106 from the patient's peritoneal cavity. A portion or all of the fluid may then be filtered, a portion drained and discarded, and replaced with fresh dialysis fluid. The used fluid, with a portion of fresh, is then pumped 107 back to the patient, wherein most, or at least about half, of the fluid returned to the patient is spent or used dialysate, the remainder being fresh dialysate. When the procedure is finished, the spent dialysis fluid is drained 108 from the patient and discarded.

The three-way valves described above are easily implemented in a number of ways. One way is to manufacture a disposable, or disposable cassette, that otherwise manages fluid flow for dialysis. Suitable three-ways valves include the one shown in FIGS. 11-12, which depicts a single three-way valve, split down the center in both the longitudinal and the cross-ways directions so that details may be seen. Three-way valve 110 is molded as part of a disposable cassette, which thus forms the valve body 111, with a flexible membrane (not shown for greater clarity) on both sides. The valve connects to the patient, or to tubing for the patient, through port 119. Other embodiments may use similar configurations, but with both valves on the same side so that actuation on both sides is not required.

Figure 11:
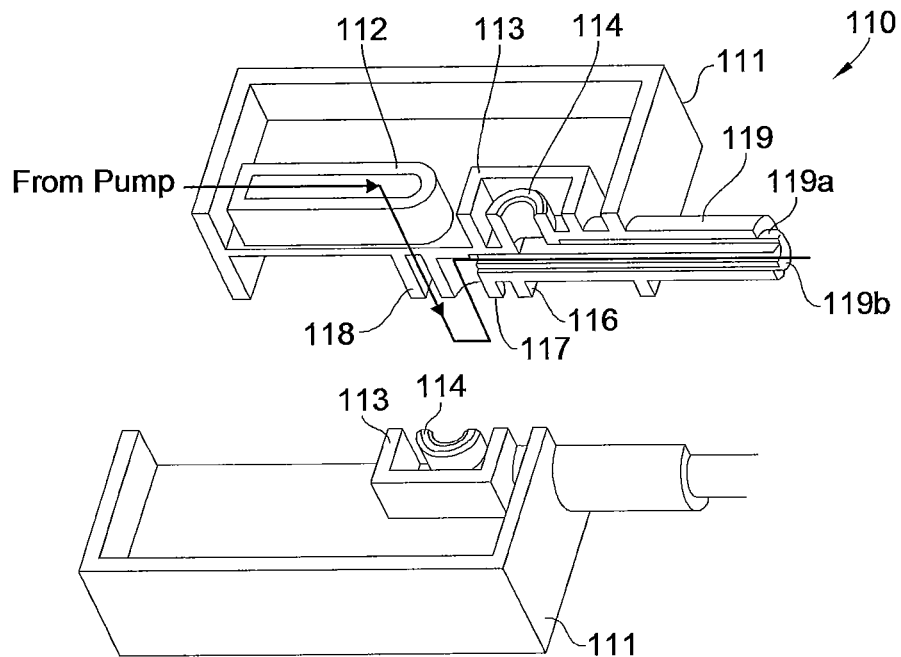
FIGS. 11-12 depict one embodiment of a 3-way, two-sided valve integrated into a disposable cassette.

The top side of valve 110 is depicted in FIG. 11, with top pump flow channel 112, top valve seat 113, and top valve 114. Flow is shown coming from a pump through top pump flow channel 112, flowing to bottom pump flow channel 118, through bottom valve 117, and out through the bottom patient flow channel 119b of patient port 119. The patient flow channels 119a, 119b connecting to port 119 are shaped as a double capital D, the Ds back to back and forming the blood input/output conduit. The connections to the appropriate portion of valve body 111 are made by cutting away a portion of the patient flow channel, forming a single D and then forming a seal along the single D as well as the double D when it is attached to a port on the valve body. Patient flow channel 119a is truncated at a matching single D socket within port 119, sealing flow channel 119a to the port and allowing fluid in channel 119a to flow to or from top valve 114. This is best seen in FIG. 11.

Figure 12:
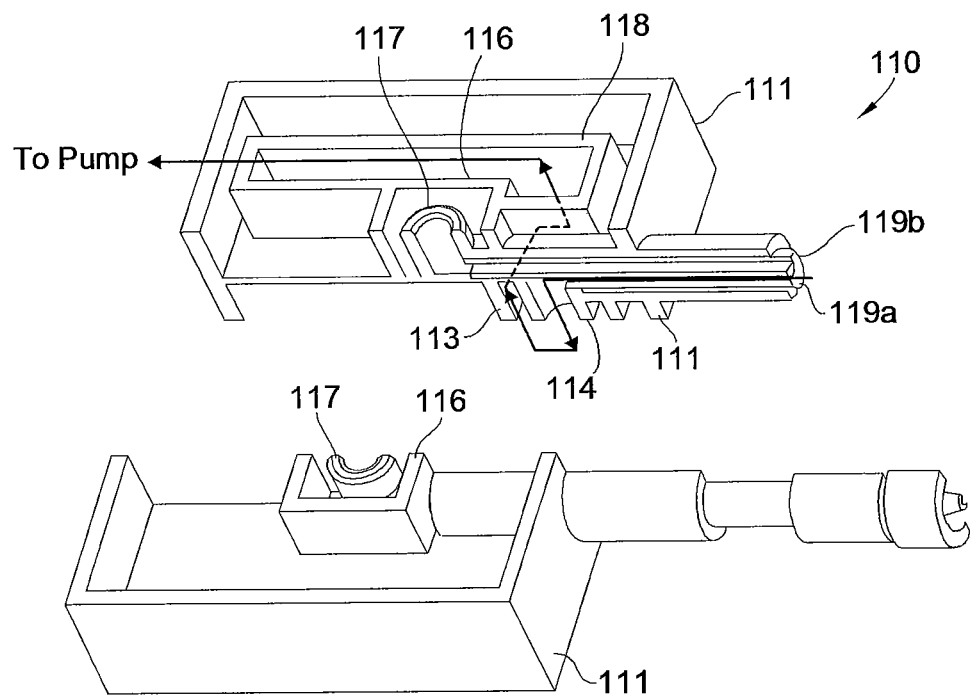

As seen in FIGS. 11 and 12, patient flow channel 119b is not truncated and extends further into port 119 and also mates with a single D sealing socket, sealing patient flow channel 119b to bottom valve 117. This allows fluid to or from valve 117 to flow in patient flow channel 119b. Port 119 connects to arterial and venous channels in needles or a catheter for a hemodialysis or peritoneal dialysis patient. The connection to the patient may also include an interface, such as a pointed or staggered end for connection to the patient, e.g., through the needles, the catheter, an arteriovenous fistula or other device. FIGS. 11 and 12 each depict a single three-way valve. Two three-ways valves are needed for the embodiments described above for FIGS. 1-6.

FIG. 12 depicts the same valve 110 turned upside down, and with the flow reversed, so that blood is entering port 119 through now-bottom patient flow channel 119a, into now under-side flow-channel 113 and through now under-side valve 114, through pump flow channel 118, and to the pump, as shown. FIG. 12 also depicts bottom valve seat 116, that is, the structure and walls surrounding valve 117, and pump flow channel 118, that is, the structure and walls that channel the fluid flow from valve 117. As is understood, the valves are typically opened and closed by applying positive or negative pressure to a flexible membrane that seals when it is flattened against the surface of one side or the other (or both). Port 119 may connect with a luer or other suitable connector to the venous and arterials needles. The seals may be made by any convenient method, but solvent bonding of plastic tubing to a plastic valve body works well. Materials useful for the tubing include flexible PVC and various polyolefin blends. Materials for the valve include acrylic, polycarbonate, polyphenylene ethers, ABS, and many others. Any appropriate and medically acceptable solvents for these materials may be used.

Figure 13:
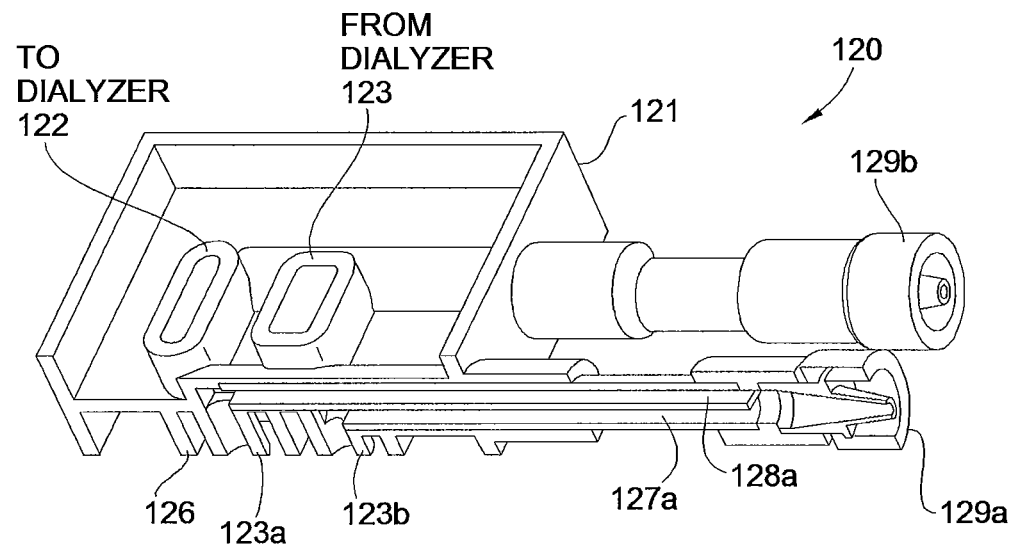
FIGS. 13-14 depict another embodiment of two, single-sided, 3-way valves integrated into a disposable cassette.
Figure 14:
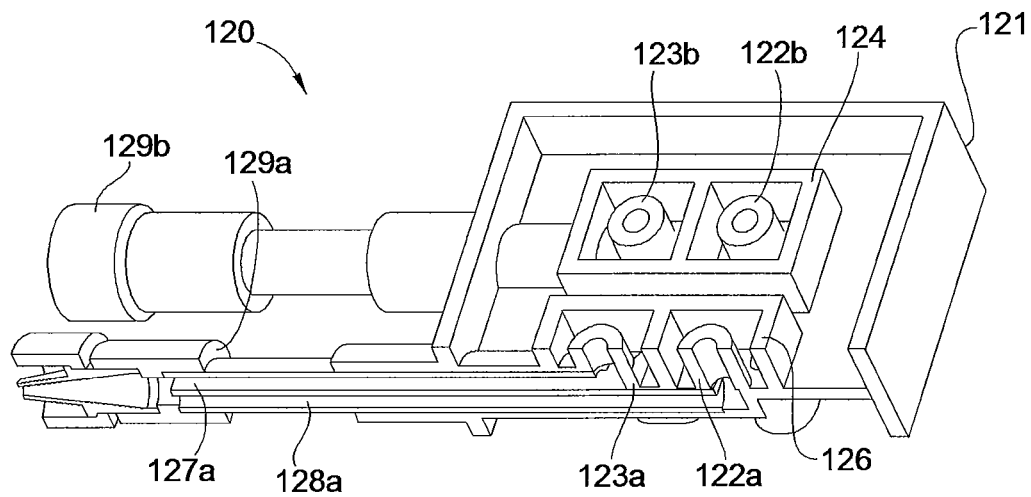

In another embodiment, dual single-needle valves may also be used, as depicted in FIGS. 13-14. A top partial cut-away view of dual single-needle valve 120 is shown in FIG. 13, with a bottom partial cut-away view of the same valve in FIG. 14. First port 129a will be connected to the patient's arterial access and second port 129b will be connected to the patient's venous access. The ports include flow connectors that interface to the patient as well as two D-shaped internal flow channels. Other shapes may be used. Within the valve body, one pump flow channel 122, shown with an ovate or elliptical cross-section connects to the inlet to the dialyzer, while the other pump flow channel, 123, shown with a rounded rectangular cross-section, connects to the outlet from the dialyzer. It is understood that these shapes may be varied and may be the same cross-sectional shape or may be different. The patient flow channels, 127a, 128a may be D-shaped as shown, or may be another desired shape.

In this embodiment, a flexible membrane (not shown for clarity) on the bottom side only is sufficient to operate the four ports of the valve, as seen in the bottom view, FIG. 14. The top side of valve 120 includes valve body 121, first (arterial) port 129a, and second (venous) port 129b. Valve 122a connects the flow of blood between the patient's arterial access and the inlet of the dialyzer, while valve 123a connects the flow of blood between the patient's arterial access and the outlet of the dialyzer. Valve 122b connects the flow of blood between the patient's venous access and the outlet from the dialyzer, while valve 123b connects the flow of blood between the patient's venous access and inlet to the dialyzer.

As shown in FIG. 13, valve body 122 allows access to the dialyzer to valves 122a, 122b, while valve body 123 allows access from the dialyzer to valves 123a, 123b. By opening and closing the desired valves, blood flows in only the desired paths to and from the patient and to and from the dialyzer, and can be reversed. For example, if valve 122a is open, blood can flow from the patient's arterial access through channel 127a to valve 122a, through valve seat 122 and its flow channel to the dialyzer (not shown). In practice, the blood may flow through a blood pump rather than directly to the dialyzer. Using an encoder on the pump motor, or other device to track flow, the pump may fill the dialyzer and the interconnecting lines until the blood flow returns to port 123 (from the dialyzer). If valves 123a, 123b are closed, the blood cannot return to the patient. If it is desired to reverse the flow of blood, valve 122a is then closed. Valve 123a and 122b are opened, valve 123a allowing flow of arterial blood to the bottom of the dialyzer and valve 122b allowing flow from the top of the dialyzer to the patient's venous access.

The back-to-back D sections of the patient flow channels are more easily seen in FIGS. 13-14. In FIG. 13, flow channel 128a seals to valve 123a while adjacent (back-to-back) flow channel 127a seals to valve 123b. In FIG. 14, the two channels meet in port 129a. In this configuration, arterial blood from the patient flows into port 129a and is returned to the patient through port 129b. Within valve 120, the arterial blood can be directed through valve 122a or 123a, depending on which valve is open. The seals may be made by any convenient method, but solvent bonding of plastic tubing to a plastic valve body works well. Materials useful for the tubing include flexible PVC and various polyolefin blends. Materials for the valve include acrylic, polycarbonate, polyphenylene ethers, ABS, and many others. Any appropriate and medically acceptable solvents for these materials may be used.

Many of the techniques described above are applicable to hemodialysis, in which blood of a patient is treated outside the body. The same technique of using renal failure therapy fluid more than once may also be applied to peritoneal dialysis, in which the patient's peritoneum may be considered to be a dialyzer, but without the necessity of providing vascular access and without having to provide extracorporeal treatment of the patient's blood.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A dialysis system, comprising:
a dialyzer having dialysis fluid inlet and outlet ports;
a blood pump connected to the dialyzer for pumping blood from a patient;
at least one drip chamber in series with the dialyzer;
a first multi-position valve for connection between the patient and the blood pump;
a second multi-position valve for connection between the patient and the drip chamber, wherein the first valve and the second valve are capable of connection in a first position for the first valve to allow a flow of blood from the patient to the blood pump and the second valve to allow a flow of the blood from the drip chamber to the patient, and are capable of connection in a second position for the second valve to allow a flow of blood from the patient to the blood pump and the first valve to allow a flow of the blood from the drip chamber to the patient;
at least one source of fresh pre-mixed dialysis fluid in fluid communication with the dialysis fluid inlet port;
a pump connected with the at least one source of the fresh pre-mixed dialysis fluid;
interconnecting lines between the patient and the valves for drawing blood from the patient and returning the blood to the patient;
a connection from the dialysis fluid outlet port to the dialysis fluid inlet port that allows recirculation of spent dialysis fluid from the outlet port to the inlet port; and
a controller programmed to cause (i) a flow of spent dialysis fluid that has passed through the dialyzer to be directed through the connection and mixed with a flow of fresh pre-mixed dialysis fluid from the at least one source, and (ii) the mixed flow of spent dialysis fluid and fresh pre-mixed dialysis fluid to be directed to the dialysis fluid inlet port, such that a number of passes of spent dialysis fluid through the dialyzer is set by a ratio of a flow of spent dialysis fluid within the dialyzer to the flow of fresh pre-mixed dialysis fluid, the ratio low enough that the fresh pre-mixed dialysis fluid from the at least one source is used during therapy.

2. The dialysis system of claim 1, wherein the dialysis fluid outlet port connects to the dialysis fluid inlet port through a flow channel or a flow balancing system.

3. The dialysis system of claim 1, further comprising a balancing system operably connected to the at least one source of fresh pre-mixed dialysate dialysis fluid and to the dialyzer for balancing a flow of dialysate dialysis fluid to and from the dialyzer.

4. The dialysis system of claim 1, further comprising a filter operably connected between the dialysis fluid outlet and inlet ports.

5. The dialysis system of claim 1, further comprising a used dialysis fluid pump.

6. The dialysis system of claim 5, wherein at least one of the pumps is a peristaltic pump.

7. The dialysis system of claim 1, wherein the interconnecting lines between the patient and the valve are configured for simultaneous withdrawal and return of blood to the patient, or for sequential withdrawal and return of the blood.

8. The dialysis system of claim 1, wherein the ratio is less than 10:1.

9. The dialysis system of claim 1, wherein the ratio is 4:1.

10. A dialysis system, comprising:
a dialyzer having dialysis fluid inlet and outlet ports;
a blood pump connected to the dialyzer for pumping blood from a patient;
at least one drip chamber in series with the dialyzer;
a plurality of valves, the valves in a first condition allowing blood to be pumped from the patient to the blood pump and from the blood pump through the dialyzer and drip chamber back to the patient;
at least one source of fresh pre-mixed dialysis fluid in fluid communication with the dialysis fluid inlet port;
a fresh dialysis fluid pump connected fluidly with the at least one source of the fresh pre-mixed dialysis fluid and the dialysis fluid inlet port;
a spent dialysis fluid pump connected fluidly to the dialysis fluid outlet port;
a connection from the dialysis fluid outlet port to the dialysis fluid inlet port that allows recirculation of spent dialysis fluid from the outlet port to the inlet port to be pumped by at least the spent dialysis pump; and
a controller programmed to cause (i) a flow of spent dialysis fluid that has passed through the dialyzer to be directed through the connection and mixed with a flow of fresh pre-mixed dialysis fluid from the at least one source, and (ii) the mixed flow of spent dialysis fluid and fresh pre-mixed dialysis fluid to be directed to the dialysis fluid inlet port, such that a number of passes of spent dialysis fluid through the dialyzer is set by a ratio of a flow of spent dialysis fluid within the dialyzer to the flow of fresh pre-mixed dialysis fluid, the ratio low enough that the fresh pre-mixed dialysis fluid from at least one source is used during therapy.

11. The dialysis system of claim 10, wherein the dialysis fluid outlet port connects to the dialysis fluid inlet port through a flow channel or a flow balancing system.

12. The dialysis system of claim 10, which is configured for simultaneous withdrawal and return of blood to the patient, or for sequential withdrawal and return of the blood.

13. The dialysis system of claim 10, wherein the ratio is less than 10:1.

14. The dialysis system of claim 10, wherein the ratio is 4:1.

15. The dialysis system of claim 1, wherein the controller is configured such that the number of passes of spent dialysis fluid through the dialyzer is set by the ratio of the flow of spent dialysis fluid within the dialyzer to the flow of fresh pre-mixed dialysis fluid, independent of any ultrafiltrate removal.

* * * * *